United States Patent
Stuart

(10) Patent No.: US 6,268,140 B1
(45) Date of Patent: Jul. 31, 2001

(54) COMBINATORIAL METABOLIC LIBRARIES

(75) Inventor: W. Dorsey Stuart, San Francisco, CA (US)

(73) Assignee: Neugenesis, San Carlos, CA (US)

( * ) Notice: Subject to any disclaimer, the term of this patent is extended or adjusted under 35 U.S.C. 154(b) by 0 days.

(21) Appl. No.: 09/310,398

(22) Filed: May 12, 1999

Related U.S. Application Data

(63) Continuation-in-part of application No. 09/214,699, filed on Jan. 8, 1999, which is a continuation-in-part of application No. 08/678,462, filed on Jul. 9, 1996, now Pat. No. 5,683,899, which is a continuation-in-part of application No. 08/191,337, filed on Feb. 3, 1994, now Pat. No. 5,643,745.

(51) Int. Cl.$^7$ .................. C12Q 1/68; C12N 1/15

(52) U.S. Cl. ............ 435/6; 435/254.11; 435/254.21; 435/254.3; 435/254.4; 435/254.5; 435/320.1; 435/440; 435/171

(58) Field of Search .................. 435/6, 254.11, 435/254.21, 254.3, 254.4, 254.5, 320.1, 440, 171

(56) References Cited

U.S. PATENT DOCUMENTS

| | | |
|---|---|---|
| 4,486,533 | 12/1984 | Lambowitz . |
| 4,816,405 | 3/1989 | Yelton et al. . |
| 4,885,249 | 12/1989 | Buxton et al. . |
| 4,935,340 * | 6/1990 | Baltz et al. ........................ 435/6 |
| 4,935,349 | 6/1990 | McKnight et al. . |
| 5,643,763 * | 7/1997 | Dunn et al. .................. 435/91.1 |
| 5,712,146 | 1/1998 | Khosla et al. . |

FOREIGN PATENT DOCUMENTS

| | | |
|---|---|---|
| 0409156 | 1/1991 | (EP) . |
| 0812914 | 12/1997 | (EP) . |
| WO 95/21263 | 8/1995 | (WO) . |
| WO 96/34112 | 10/1996 | (WO) . |
| WO 96/40968 | 12/1996 | (WO) . |
| WO 97/35966 | 10/1997 | (WO) . |
| WO 98/01534 | 1/1998 | (WO) . |

OTHER PUBLICATIONS

Arnaise, S. et al., Heterologous Expression Of Mating–Type Genes In Filamentous Fungi, Proc. Natl. Acad. Sci. USA (1993) 90:6616–6620.

Bartel, P. L. et al., Biosynthesis Of Anthraquinones By Interspecies Cloning Of Actinorhodin Biosynthesis Genes In Streptomycetes: Clarification Of Actinorhodin Gene Functions, J. Bacteriol. (1990) 172 (9):4816–4826.

Buczynski, S. et al., Expression And Secretion Of Human Antibody Light And Heavy Chains In Neurospora Crassa, Fungal Genetics Newsletter–Abstracts From the 18th Fungal Genetics Conference (1995 Suppl.) 42A:83.

Carattoli, A. et al., A Chimeric Light–Regulated Amino Acid Transport System Allows The Isolation Of Blue Light Regulator (BLR) Mutants Of Neurospora Crassa, Proc. Nat. Acad. Sci. USA (1995) 92:6612–6616.

Carú, M. et al., Molecular Cloning And Expression In Saccharomyces Cerevisiae And Neurospora Crassa Of The Invertase Gene From Neurospora Crassa, J. Appl. Bacteriol. (1989) 67:401–410.

Connerton, I.F. et al., Comparison and Cross–Species Expression Of The Acetyl–CoA Synthetase Genes Of The Ascomycete Fungi, Aspergillus Nidulans and Neurospora Crassa, Molecular Microbiology (1990) 4(3):451–460.

Dalbey, R. E. et al., Signal Peptidases In Prokaryotes and Eukaryotes—A New Protease Family, TIBS (1992) 17:474–478.

Davis, R. H. et al., Genetic And Microbiological Research Techniques For Neurospora Crassa, Methods in Enzymology (1970) 17A:79–143.

Haas, F. et al., A Series Of Histidineless Mutants Of Neurospora Crassa, Genetics (1952) 37:217–26.

Hiett, K.L. et al., Induced Expression Of The Aspergillus Nidulans QUTE Gene Introduced By Transformation Into Neurospora Crassa, Mol. Gen. Genet. (1990) 222:201–205.

Hopwood, D.A. et al., Production Of 'Hybrid' Antibiotics By Genetic Engineering, Nature (1985) 314(18):642–644.

Khosla, C. et al., Genetic Construction And Functional Analysis Of Hybrid Polyketide Synthases Containing Heterologous Acyl Carrier Proteins, J. Bacteriol. (1993) 175(8):2197–2204.

Koo, K. et al., Sequence And Structure Of mtr, An Amino Acid Transport Gene Of Neurospora Crassa, Genome (1991) 34:644–651.

Lambowitz, A. M. et al., Mitochondrial Ribosome Assembly In Neurospora, J. Cell Biology (1979) 82:17–31.

MacKenzie, D.A. et al., Regulation Of Secreted Protein Production By Filamentous Fungi: Recent Developments And Perspectives, J. Gen. Microbiol. (1993) 139:2295–2307.

Malpartida, F. et al., Molecular Cloning Of The Whole Biosynthetic Pathway Of A Streptomyces Antibiotic And Its Expression In A Heterologous Host, Nature (1984) 309(31):462–464.

Nakano, E. T. et al., Expression Vectors For Neurospora Crassa And Expression Of A Bovine Preprochymosin cDNA, Fungal Genetics Newsletter (1993) 40:54–56.

(List continued on next page.)

Primary Examiner—James Ketter
(74) Attorney, Agent, or Firm—Morrison & Foerster LLP

(57) ABSTRACT

The present invention provides methods and compositions for producing and screening combinatorial metabolic libraries of multimeric proteins. The present invention relies on the use of filamentous fingal heterokaryons that are produced using two or more parent strains into which a population of heterologous nucleic acids encoding components of a metabolic pathway have been introduced.

22 Claims, No Drawings

OTHER PUBLICATIONS

Patel, B. et al., Evidence For The Expression Of The E. Coli Ch1M Nitrate Gene In N.Crassa, J. Cell. Biochem.–Abstracts (1985) Suppl. 9C:172.

Peberdy, J.F., Protein Secretion In Filamentous Fungi—Trying To Understand A Highly Productive Black Box, Tibtech (1994) 12:50–57.

Perkins, D. D. et al., Chromosomal Loci Of Neurospora Crassa, Microbiological Reviews (1982) 46(4):426–570.

Puetz, D., Expression Of Aspergillus Nidulans OTS Gene In Neurospora Crassa, Neurospora Newsletter (1984) 61:17.

Rasmussen–Wilson, S.J. et al., Expression Of A Plant Protein By Neurospora Crassa, Appl. Environ. Microbiol. (1997) 63(9):3488–3493.

Sachs, M.S. et al., Expression Of Herpes Virus Thymidine Kinase In Neurospora Crassa, Nucleic Acids Res. (1997) 25(12):2389–2395.

Sherman, D. H. et al., Functional Replacement Of Genes For Individual Polyketide Synthase Components In Streptomyces Coelicolor A3(2) By Heterologous Genes From A Different Polyketide Pathway, J. Bacteriol. (1992) 174:6184–6190.

Stuart, W.D. et al., Cloning Of mtr, An Amino Acid Transport Gene Of Neurospora Crassa, Genome (1988) 30:198–203.

Vollmer S.J. et al., Efficient Cloning Of Genes Of Neurospora Crassa, Proc. Natl. Acad. Sci. USA (1986) 83:4869–73.

Yamashita, R.A. et al., The Expression Of Porcine Relaxin In Neurospora Crassa, Fungal Genetics Newsletter (1995 Suppl.) 42A(Abstract #31):54.

* cited by examiner

COMBINATORIAL METABOLIC LIBRARIES

RELATED APPLICATIONS

The present application is related to U.S. Ser. No. 09/214,699, filed Jan. 8, 1999, which is a 371 national phase application of U.S. Ser. No. 08/678,462, filed Jul. 9, 1996, now U.S. Pat. No. 5,683,899, which is a continuation-in-part of U.S. Ser. No. 08/191,337, filed Feb. 3, 1994, now U.S. Pat. No. 5,643,745, all of which are hereby incorporated by reference in their entireties, as if fully set forth.

FIELD OF THE INVENTION

The present invention relates to the field of molecular biology and the production of a population of cells expressing heterologous gene products necessary for conducting various metabolic activities. The present invention provides methods and compositions relating to a population of heterokaryonic filamentous fingal cells that produce proteins and other gene products encoded by heterologous nucleic acid sequences, such that a library of combinatorial metabolic pathways is expressed in the cells. Heterokaryon members of this libraries may be isolated and used for the production of primary and secondary metabolites as well as for any resultant catabolic activity.

BACKGROUND ART

The cloning and expression of heterologous genes in fungi has been used to produce a variety of useful proteins. For example: Lambowitz, U.S. Pat. No. 4,486,533, discloses the autonomous replication of DNA vectors for filamentous fungi by mitochondrial plasmid DNA and the introduction and expression of heterologous genes into Neurospora; Yelton et al., U.S. Pat. No. 4,816,405, discloses tools and systems that enable the modification of important strains of filamentous ascomycetes to produce and secrete large quantities of desired heterologous proteins; Buxton et al., U.S. Pat. No. 4,885,249, discloses the transformation of *Aspergillus niger* by a DNA vector that contains a selectable marker capable of being incorporated into the host *A. niger* cells; and McKnight et al., U.S. Pat. No. 4,935,349, discloses a method for expressing higher eukaryotic genes in Aspergillus involving promoters capable of directing the expression of a heterologous gene in Aspergillus and other filamentous fungi. Similar techniques have been used to clone the mtr gene involved with amino acid transport in *Neurospora crassa* ("*N. crassa*") and to verify the tight linking of the cloned DNA to genomic markers flanking this gene in vivo. Stuart, W. D. et al., Genome (1988) 30:198–203; Koo, K. and Stuart, W. D. Genome (1991) 34:644–651.

Filamentous fungi possess many characteristics which make them good candidates for use in producing eukaryotic proteins. Filamentous fungi can secrete complex proteins; correctly fold three dimensional proteins including disulfide bond formation; proteolytically clip proteins following translation; and glycosylate proteins using n-linked and o-linked glycosylation reactions. These abilities have made this group of organisms attractive hosts for the production of secreted recombinant proteins. (MacKenzie, D. A. et al., *J Gen Microbiol* (1993) 139:2295–2307; Peberdy, J. F., *Trends in BioTechnology* (1994) 12:50–57).

*Neurospora crassa* has been used as a host cell for recombinant production of homologous and heterologous proteins such as those from mammals (see Yamashita, R. A. et al., *Fungal Genetics Newsletter* (1995 Suppl.) 42A for porcine relaxin; Kato, E. et al., *Fungal Genetics Newsletter* (1995 Suppl.) 42A for mammalian thrombolytic protein (mTh); Buczynski, S. et al. *Fungal Genetics Newsletter* (1995 Suppl.) 42A for human antibody light and heavy chains; and Nakano, E. T. et al. *Fungal Genetics Newsletter* (1993) 40:54–56 for bovine preprochymosin), plants (see Rasmussen-Wilson, S. J. et al., Appl. Environ. Microbiol. (1997) 63:3488–3493 for zeamatin from corn); fungi (see Carattoli, A., et al., *Proc Nat Acad Sci USA* (1995) 92:6612–6616 for neutral amino acid permease gene mtr expression; Puetz, D. *Neurospora Newsletter* (1984) 31:17 for ornithine transcarbamylase (OTS); Caru, M. et al. J. Appl. Bacteriol. (1989) 67:401–410 for invertase; Connerton, I. F. et al. Molec. Microbiol. (1990) 4:451–460 for acetyl-CoA synthetase with introns correctly spliced out; Arnaise, S. et al. *Proc Nat Acad Sci USA* (1993) 90:6616–6620 for mating-type genes; Hiett, K. L. et al. Mol. Gen. Genet. (1990) 222:201–205 for catabolic dehydroquinase, QUT E gene; and Weiss, R. L. et al. Gene Manipulations in Fungi, Academic Press Inc.:New York, pp. 280–292 (1985) for a review of expressing *A. nidulans* gene products), bacteria (see Patel, B. et al., J. Cell. Biochem. (1985) Suppl. 9C:172 (Abstr.) for the *E. coli* Ch1M nitrate gene), and mammalian viruses (see Sachs, M. S. et al., Nucleic Acids Res. (1997) 25:2389–2395 for herpes virus thymidine kinase).

Moreover, such recombinant protein production has occurred in Neurospora crassa via expression from heterologous promoters, such as that from Aspergillus (see Weiss et al., Supra), Podospora anserina (see Amaise et al., Supra), and a mammalian viral promoter (see Sachs et al., Supra), all of which suggests that Neurospora crassa can utilize regulatory elements of heterologous genes.

Additionally, Neurospora crassa has recently been used as a host cell for expressing recombinant heterodimeric and multimeric proteins by means of a heterokaryon., PCT Application WO 95/21263. A "heterokaryon" (or a heterokaryonic cell) is a cell formed from the fusion of two filamentous fungal parent strains, each heterokaryon cell thus containing two (or more) genetically different nuclei. Heterokaryons contain nuclei from two parent strains that are generally homozygous for all heterokaryon compatibility alleles (except for the mating type allele when the tol gene is present). At least ten chromosomal loci have been identified for heterokaryon incompatibility: het-c, het-d, het-e, het-i, het-5, het-6, het-7, het-8, het-9 and het-10, and more are inferred to exist. Perkins et al., "Chromosomal Loci of *Neurospora crassa*", *Microbiological Reviews* (1982) 46:426–570, at 478.

Aside from the expression of useful gene products, recombinant expression has been used to produce products resulting from a metabolic pathway, i.e. from the action of a number of gene products. For example, a diverse variety of polyketide synthases constitute various pathways for the production of the large family of polyketides, some of which have antibiotic or other pharmacological properties. Thus genes encoding the various polyketide synthases necessary for the production of particular polyketides, such as actinorhodin and aloesaponarin, have been recombinantly expressed in heterologous host cells (see Malpartida et al. Nature (1984) 309:462; Bartel et al. J. Bacteriol. (1990) 172:4816–4826). Moreover, host cells expressing hybrid polyketide synthases and hybrid polyketides have also been constructed (see Khosla et al. J. Bacteriol. (1993) 175:2197–2204; Hopwood et al. Nature (1985) 314:642–644; Sherman et al. J. Bacteriol. (1992) 174:6184–6190; U.S. Pat. No. 5,712,146).

Other metabolic pathways of interest in the art include those that produce primary and secondary metabolites as well as those that result in useful catabolic activities. Primary and secondary metabolites are respectively defined as those involved in the metabolic processes central to most cells and those involved in specialized cellular processes. Examples of primary metabolites are components involved in cellular biosynthetic machinery, energy production or utilization, and the turnover of cellular constituents, while secondary metabolites include substances such as antibiotics, anti-tumor or anti-cancer agents, anti-fungal agents, mating factors or pheromones, terpenes, toxins, alkaloids, biodegradable plastics, pigments, signaling molecules, cell surface molecules, secreted molecules, and numerous others. Useful catabolic activities include degradation or detoxification of waste materials, desulfurization of petroleum, and the breakdown of large or complex molecules such as cellulose or lignin.

The present invention advances the work of that disclosed in PCT Application WO 95/21263 by providing methods and compositions for producing a population of cells expressing heterologous gene products necessary for producing various metabolites and conducting various metabolic activities. Preferably, the cells are heterokaryonic filamentous fungi. Such methods and compositions are useful in the production of known products, such as proteins, nucleic acids and other metabolites, as well as the discovery and production of novel metabolites by the constitution of a novel combinatorial metabolic pathway in the cells.

SUMMARY OF THE INVENTION

The present invention provides panels of heterokaryon filamentous fungi that express known and novel, gene products and metabolites as well as express known or novel catabolic pathways; methods for generating panels of heterokaryon filamentous fungus that express these gene products, metabolites and pathways; methods of screening panels of heterokaryon filamentous fungus that express these gene products, metabolites and pathways; kits containing panels of heterokaryon filamentous fungus that express these gene products, metabolites and pathways; methods of using panel members as producers of useful metabolites or as catabolic (degradative) agents; and methods of using panel members to isolate nucleic acid sequences encoding components of a metabolic pathway.

The heterokaryon panels of the present invention are generated by fusing two or more parent fungal strains, each parent strain containing the necessary markers to maintain a heterokaryonic state as well as an expression unit that contains a heterologous nucleic acid, where the heterologous nucleic acid encodes one or more gene products under the control of regulatory elements naturally associated with them or under the control of heterologous regulatory elements introduced by recombinant means. Thus the heterokaryon panels comprise a combinatorial library of metabolic pathways resulting from various combinations of heterologous nucleic acids as well as combinations with the gene products endogenous to the host cell. These heterokaryon panels are useful in providing a method of generating heterogeneity in metabolic pathways by permitting a large variety of different combinations of heterologous nucleic acids encoding one or more pathway components.

By appropriately selecting or randomizing the combination of heterologous nucleic acids, each heterokaryon will result in the expression of all or part of a known or novel metabolic pathway. Application of appropriate screening and/or selection methods to the panels will identify heterokaryons possessing desirable metabolic pathways based on the production of a primary or secondary metabolite, which includes increased production of a metabolite endogenous to the host fungal strain, or based on a gain of catabolic activity, which includes increased catabolic activity endogenous to the host fungal strain. Aside from standard screening methods, members of the heterokaryon panels can also contain a reporter construct or selection marker sensitive to the production of a particular metabolite or catabolic breakdown product. Alternatively, the panels can be screened with a reporter molecule sensitive to the presence of a particular metabolite or catabolic activity. Moreover, and in addition to identification based on metabolic activity, the panels can be screened and/or selected for viability under various growth and environmental conditions, such as but not limited to temperature, nutrient source, pH, humidity, oxygen concentration, light, physical (like UV) or chemical mutagens, toxic agents, and osmolarity/salinity, conferred by expression of the heterologous nucleic acids.

The identified heterokaryons are useful based on their metabolic activity to either be producers of desirable metabolites or as an actual catabolic agent to degrade particular substrates. Moreover, a heterokaryon can be used to isolate and clone nucleic acids encoding previously unidentified components of a metabolic pathway.

Thus the invention relates to the expression of all or part of a combinatorial metabolic pathway in a host cell, such as a heterokaryonic fungus, wherein the pathway results from the combination in the host cell of one or more known, unidentified or random nucleic acids, from one or more heterologous sources. The heterologous sources include animals, plants, microorganisms, and viruses. They may also be known organisms or a mixture of known or unidentified organisms found in nature. The resultant metabolic pathway, or portion thereof, may be identical or different from pathways known in the art or endogenous to the host cell, and may be identical to, or a mere increase of, a pathway endogenous to the host cell. The pathway may result solely from the expression of the heterologous nucleic acids or from the combination of the heterologous gene products with components, such as gene products or other metabolites, normally found in the host cell. Moreover, the resultant pathways may produce a known or novel metabolite or result in a metabolism that can degrade one or more substrates.

The combinatorial metabolic pathways of the invention include those that are unknown in the art or are normally silent or undetectable. Additionally, the invention includes the use of heterologous nucleic acids subjected to intentional modification or mutagenesis, such as substitutions, insertions and deletions, prior to their introduction into a host cell to form a combinatorial metabolic pathway.

Based on the above, the present invention provides panels of heterokaryons that express various metabolic pathways to produce various metabolites and impart various catabolic activities, methods of producing a panel of heterokaryons that express these metabolic pathways, methods of screening a panel of heterokaryons that express these pathways, kits that contain a panel of heterokaryons that express these pathways, methods of using panel members to produce particular metabolites or as catabolic catalysts, and methods of using panel members to isolate nucleic acid molecules that encode components of a metabolic pathway.

DETAILED DESCRIPTION OF THE PREFERRED EMBODIMENTS

The present invention provides novel methods and compositions for expressing a combinatorial metabolic pathway in a host cell. The pathways are generated from the expression of one or more known or random heterologous nucleic acids from one or more sources. To obtain host cells expressing combinatorial metabolic pathways, a panel of heterokaryons is produced by a method comprising the steps of introducing heterologous nucleic acids into fungal host cells to form recombinants, and then forming a panel of heterokaryonic fungal strains using one or more of the recombinants. The heterologous nucleic acids may be from any eukaryote, prokaryote, virus or bacteriophage of interest and may contain regions encoding one or more components of a metabolic pathway or part thereof. The heterologous nucleic acid may also contain naturally present regulatory elements.

The panel of heterokaryons can then, if appropriate, be cultured under conditions in which the heterologous nucleic acids are expressed and screened for the expression of a combinatorial metabolic pathway. Screening methods include the detection of a desirable primary or secondary metabolite or the existence of a desirable catabolic activity. Each of the elements, namely the fungal parents, the heterologous nucleic acids, the fusion methods, the culturing conditions, and the screening methods are described in detail below. Particularly, when using the present methods for the production of a combinatorial metabolic pathway, the parent strains used in making the heterokaryon each contain a population of cells, each cell expressing one or more heterologous nucleic acids.

Nature of Filamentous Fungi and Background Requirements for Heterokaryon Formation Fungi can occur in single mononucleated cells that yield filamentous multinuclear strands, yeast cells, fruiting bodies with diverse spores, and/or cells that are differentiated sexually. They can also exist in multinucleated forms. The principal element of the growing form of a fungus as a mold is the hypha, a branching tubular structure, about 2 $\mu$m–10 $\mu$m in diameter. Hyphae grow by elongation at their tips (apical growth) and by producing side branches. Thus, as a colony grows, its hyphae form a mass of intertwining strands.

Some hyphae penetrate into the culture medium on which the fungus is growing to absorb nutrients, while those hyphae that project above the surface of the medium constitute an "aerial mycelium." Most colonies grow at the surface of liquid or solid media as irregular, dry, filamentous mats. In most species, the hyphae are divided by cross-walls called "septa." These septa, however, have fine, central pores. Thus, even septate hyphae have nuclei that are embedded in a continuous mass of cytoplasm and, in effect, contain a multiplicity of nuclei in a transportable cytoplasm.

The term "filamentous fungi" refers to those fungi that can form a mycelium through a mass of branching, interlocking filaments and, although interrupted by cross walls, permit the passage of cytoplasm between compartments due to perforations in the cross walls. Many of these fungi form meiotic spores within a sac when propagated sexually. With the appropriate stimulation, however, the mechanism of which is not entirely understood, reproduction can occur asexually. In this manner of reproduction, spores known as "conidia" are borne externally at the tips of budding projections formed at various locations along the filaments.

The filamentous fungi used to generate the heterokaryon panels of the present invention are generally Phycomycetes, Ascomycetes, Basidiomycetes, and Deuteromycetes. The Phycomycetes include all non-septate, as well as some septate, filamentous fungi. Their asexual spores are of various kinds and include sporangiospores contained within sacs formed at the end of specialized stalks. Different species have different sexual cycles.

Ascomycetes are distinguished from other fungi by the ascus, a saclike structure containing sexual spores, known as ascospores. The ascospores are the end product of mating, the fusion of male and female nuclei, two meiotic divisions, and usually one final mitotic division. Basidiomycetes are distinguished by sexual spores that form on the surface of a specialized structure. The Deuteromycetes are often referred to as "imperfect fungi" because no sexual phase has yet been observed. Their hyphae are septate, and conidial forms are similar to those of the Ascomycetes.

The preferred filamentous fungus is of the group Ascomycetes, more preferably, from the genera Neurospora, Aspergillus and Penicillium. Particularly useful species from Neurospora include *N. intermedia, N. crassa, N. sitopula,* and *N. tetraspora*, of which the most preferred species is *N. crassa*. Useful species of Aspergillus include *A. nidulans, A. niger, A. terreus,* and *A. fumegatus*.

The vegetative growth of filamentous fungi involves nuclear division with cell division (mitosis). This type of cell division consists of asexual reproduction, i.e., the formation of a new clone without the involvement of gametes and without nuclear fusion by way of conidia. For example, the species of Neurospora contain in their nuclei seven different chromosomes, each having a single copy, i.e., the vegetative organism is haploid. This haploid state is typically maintained during mycelial growth and during asexual reproduction through the formation of conidia.

Sexual reproduction can also occur, and then two haploid cells (hyphae or conidia) of different mating type fuse to form a dikaryotic cell containing two distinct nuclei. The two haploid nuclei thus coexist in the same cytoplasm and, for a time, divide more or less in synchrony. If a cell initiates ascospore formation, however, the two different haploid nuclei can actually fuse to form a diploid nucleus, which contains pairs of homologous chromosomes. This diploid cell then begins meiosis.

A "heterokaryon" (or a heterokaryonic cell) is a cell with two (or more) genetically different nuclei. The heterokaryons of the invention must contain nuclei from cells that are homozygous for all heterokaryon compatibility alleles (except for the mating type allele when the tol gene is present). At least ten chromosomal loci have been identified for heterokaryon incompatibility: het-c, het-d, het-e, het-i, het-5, het-6, het-7, het-8, het-9 and het-10, and more are inferred to exist. Perkins et al., "Chromosomal Loci of *Neurospora crassa*", *Microbiological Reviews* (1982) 46:426–570, at 478.

If two strains carry different alleles at one or more het loci, they are unable to form stable heterokaryons. Protoplasmic killing occurs after fusion of unlike hyphae or after microinjection of cytoplasm or extracts into unlike strains. When duplications (partial diploids) are heterozygous for het one or more alleles, growth is inhibited and highly abnormal. A number of heterokaryon incompatibility loci (specifically, het-c, -d, -e, and -i) were first defined by heterokaryon tests. Het-5 through -10 loci were detected by using duplications, as differences at het loci are common in natural populations. Id.

Mating type alleles "A" and "a" also act as het genes in *N. crassa*, although some slow heterokaryotic growth may occur. Microinjection experiments have implicated proteins in the killing reaction. Thus, opposite mating types are also generally important for the complex events associated with the proliferation of heterokaryotic ascogenous hyphae. Id. at 436 and 478. However, if the tol gene is present, the vegetative (heterokaryon) incompatibility associated with opposite mating type alleles A and a is suppressed without sexual compatibility being affected. Thus, (tol; A+a; a) heterokaryons can be fully compatible and stable if the other het loci are homokaryotic and A/a duplications grow normally when the tol gene is present.

If hyphae from two different strains that are homozygous for the compatibility loci are provided, they may fuse when grown in the same medium, in particular when fusion is forced as described below. The resulting culture will then contain nuclei from both strains circulating in the shared cytoplasm of a common mycelial mat.

The methods and compositions of the present invention provide and use a panel of heterokaryons. As used herein, a "panel of heterokaryons" refers to an array of two or more heterokaryons, where each heterokaryon, or a substantial percentage thereof, expresses a different metabolic pathway, or portion thereof. As described below, the panel of heterokaryons can readily be stored or cultured in a multiwell microtiter plate for efficient screening and propagation.

Construction of Combinatorial Libraries Containing Heterologous Nucleic Acids

In describing the invention, the following terminology will be used in accordance with the definitions set out below:

The invention involves the production of a "library" or "combinatorial library" of heterokaryons expressing a "pathway" or "metabolic pathway", where the first two terms in quotes relate to a plurality of constructs comprising heterologous nucleic acids from one or more sources capable of being expressed by regulatory elements naturally found associated with the nucleic acid or heterologous regulatory elements introduced by recombinant means. Such libraries may be present in an appropriate host organism, such as filamentous fungi, able to express the heterologous nucleic acids and permit combinations of the heterologous nucleic acids to occur.

The latter two terms in quotes relate any number of associated or related biochemical reactions involving related molecules. Such pathways may be anabolic (i.e. biosynthetic) as well as catabolic (i.e. degradative), in nature to produce metabolites or result in a degradative activity. Examples of metabolic pathways include, but are not limited to, those for the synthesis of desirable metabolites such as antibiotics, anti-fungal agents, and anti-proliferative compounds as well as those for the expression of a desirable degradative activity. Preferred metabolites are secondary metabolites. Particularly preferred metabolites are those previously unknown and only available by expression of unique combinatorial metabolic pathways made possible by the invention.

"Combinatorial" indicates that the library or pathway is a combination of one or more heterologous nucleic acids with the genetic complement of the host heterokaryon. Other combinations include nucleic acids from only one heterologous source in the host heterokaryon as well as nucleic acids from one or more heterologous sources in the heterokaryonic host.

A "part" or "portion" of a metabolic pathway relates to one or more gene product(s) that participates in at least one biochemical reaction or step in the pathway.

A "component" of a metabolic pathway, or part thereof, relates to a gene product functioning in, intermediate product produced by, or final metabolite resulting from said metabolic pathway, or part thereof.

"Heterologous" relates to nucleic acids and sequences that are not normally associated with, or endogenous to, a given cell. The term also relates to nucleic acids and sequences that are not normally associated with another nucleic acid. Thus a "heterologous" nucleic acid is that which is normally not found in association with a host cell into which the nucleic acid is introduced. Similarly, a "heterologous" regulatory element is that which is normally not found in association with a nucleic acid to which the regulatory element is covalently attached, whether directly or indirectly.

A "metabolite" relates to any molecule resulting from a metabolic pathway, an intermediate reaction in a pathway, or as a by-product of such a pathway. It may be the product of a single gene product or biochemical reaction, or of a plurality of gene products and biochemical reactions.

A "nucleic acid encoding a gene product" relates to that portion of a nucleotide sequence which may be expressed, either by regulatory elements already present in the nucleic acid or when operably linked to appropriate regulatory elements, to produce a functional gene product, defined as any functional molecule resulting from the expression of a nucleic acid. Such nucleic acids can be derived from, for example, prokaryotic sequences, cDNA from eukaryotic mRNA, and genomic DNA sequences from eukaryotic DNA (such as mammalian), or may include synthetic DNA.

A nucleotide sequence is "operably linked to" regulatory elements when the latter effect the expression of the former in a host cell.

An "expression unit" relates to a nucleic acid molecule that is operably linked to regulatory elements that direct the expression of the operably linked nucleic acid in a host organism under appropriate conditions. The regulatory elements of an expression unit may be those normally found with the nucleic acid or those recombinantly introduced.

A cell has been "transformed" by exogenous nucleic acids when such exogenous nucleic acids have been introduced across the host cell membrane. For prokaryotes such as bacteria the exogenous DNA may be maintained on an episomal element such as a plasmid. Because filamentous fungi do have nuclei (are eukaryotic), most stably transformed fungus host cells contain the exogenous DNA integrated into a chromosome, so that it is inherited by daughter cells through chromosomal replication.

A "recombinant host" or "host cell" relates to cells that have been, are or will be transformed with nucleic acids prepared by recombinant techniques, and includes the cell originally transformed and cultures and progeny thereof.

A variety of methods can be employed to generate a population of heterologous nucleic acid molecules for construction of a combinatorial metabolic library. In the following, the antibiotic penicillin is used as an illustrative example. A skilled artisan can readily use the methods outlined below, or any equivalent method known in the art, to generate a combinatorial metabolic library able to express penicillin as a metabolite.

A population of nucleic acid molecules that encode components of the metabolic pathway which produces an antibiotic, such as penicillin, can be produced using standard nucleic acid manipulation/cloning techniques. For example, genomic DNA from *Penicillium notatum* or *P. chrysogenum*, the fungi which produces penicillin, can be fragmented by physical, chemical or enzymatic means to produce a population of nucleic acids. This population, which is heterologous relative to the host cell used, can be used to directly transform the host cells, such as those of a filamentous fungus, or first inserted into an expression unit before transformation. In the former case, the nucleic acid would be expressed via whatever regulatory element(s) were already associated while the latter case as nucleic acids under the control of recombinantly introduced regulatory elements. The population is expected to be integrated into the host genome when filamentous fungi are used as the host. Upon integration, there is also the possibility of the nucleic acids being under the control of adjacent host cell regulatory element(s).

The fragmentation of nucleic acids can occur by methods such as physical shearing, chemical cleavage or enzymatic hydrolysis. The size of the resultant fragments can be controlled by the particulars of the method used. For very large genomic fragments which are more likely to contain multiple prokaryotic genes or a eukaryotic gene with many large introns, physical shearing may be preferred. For other large fragments, restriction enzymes with cognate cleavage sites that occur infrequently may be used. For smaller fragments, restriction enzymes that cleave more frequently are available.

Alternatively, mRNA can be first isolated from *Penicillium notatum* or *P. chrysogenum* and then used as a template for the generation of cDNA molecules by art-known cloning methods. The populations of cDNA molecules thus produced can be inserted into a suitable expression unit as described above before transformation.

For the production of novel metabolites, heterologous nucleic acids can be prepared from other organisms for inclusion in the combinatorial metabolic library. For example, other species of the genus Penicillium, such as *P. citrinum, P. claviforme, P. expansum, P. patulum, P. griseofulvum, P. cyclopium, P. puberulum, P. pupurogenum, P. rubrum* and *P. marneffei*, produce other biologically active metabolites. Thus the inclusion of nucleic acids from these species in a combinatorial metabolic library in a filamentous fungus would result in heterokaryon panels that have different combinations of the metabolic pathway components from these various species. In other words, the pathway components encoded by various heterologous nucleic acids in the heterokaryon panels will be able to interact in vivo with host cell and other heterologous components to form a novel metabolic pathway producing novel metabolites. These panels can be screened for the production of previously unidentified metabolites, including novel antibiotics.

Additionally, heterologous nucleic acids from genera other than Penicillium can be prepared and included in combinatorial metabolic libraries to introduce yet additional combinations of metabolic pathway components into heterokaryon panels.

Moreover, site directed or random mutagenesis can be performed on any of the above mentioned heterologous nucleic acids prior to their transformation into host cells. Procedures such as random or site-directed mismatched PCR priming, linker-scanning mutagenesis, or chemical and physical mutagenesis can readily be used to generate a population of nucleic acid molecules that encode metabolic pathway components. For example, randomly generated or rationally designed PCR primers can be used to generate random or targeted heterogeneity in a protein encoding sequence.

Construction of Expression Units Containing Heterologous Nucleic Acids

The expression units containing a heterologous nucleic acid are constructed using well known techniques. In general, an expression unit is generated by placing a nucleic acid sequence into operable linkage with control sequences that direct the expression of the nucleic acid in the ultimate filamentous fungus host.

A variety of control elements are presently known in the art for directing the expression of an operably linked nucleic acid sequence in either a constitutive or inducible fashion. The choice of a control sequence will be based on the fungal strain used, conditions employed for culturing the fungus, the level of expression desired, and the nature of expression required (for example, inducible versus constitutive). A skilled artisan can readily utilize art-known control sequences for generating the expression units used in the present heterokaryon panel.

In addition to sequences that direct the transcription and translation of the protein-encoding sequence, the expression units of the present invention may further control signal sequences, expression control elements that direct the export of a protein outside the cell. A review of secretory signals that are known in filamentous fungus are provided by Dalbey R. E., et al., TIBS 17:474–478 (1992). The skilled artisan can readily generate expression units that contain secretory signals without undue experimentation.

In one application, recombination units are generated instead of the expression units. In such a use, the heterologous nucleic acid is flanked by regions of DNA that contain sequences that are homologous to an integration site in the host fingal strain. The homologous sequences are then used to stimulate and direct homologous recombination between the recombination units and the host chromosome. When recombination units are used, the host strain is preferably first transformed with an expression unit that contains an expression control element followed by sequences that are used for targeted recombination. For example, a nucleic acid encoding a known gene product involved in penicillin production can be introduced into a host fungus and then homologous recombination units can be used to introduce heterogeneity within a targeted region of the host chromosome.

Intermediate hosts are sometimes used to produce intermediate vectors capable of transforming the ultimate fungal cells. The intermediate bacterial transformants can then be grown to obtain the desired quantities of DNA, which can be used to transform a desired filamentous fungus host. Examples of commonly available bacterial vectors that can serve as intermediate vectors include, for example, pBR322, pUC8 and pUC9. Additional useful intermediate vectors include pHY201, pKBY2, pTZ18R, pX182 and pCVN2.9, pN807, pN846.

It will be understood that this description and disclosure of the invention is intended to cover all embodiments that are within the spirit and scope of the invention. For example, it is within the knowledge of the art to insert, delete or substitute amino acid encoding nucleotides of an open reading frame without substantially affecting the activity of the encoded molecule, and such gene products as can be generated with deletions, additions or substitutions to naturally occurring heterologous nucleic acids are included in the invention.

Nature of the Parent Strains

Since each of the parent fingal strains used in making the panel of heterokaryons of the present invention will contain a member of a population of heterologous nucleic acids, combinations of these strains in various heterokaryon panel members will produce all or part of various metabolic pathways. If a known number of gene products are involved in a given pathway, the heterokaryon panel members will normally contain at least that number of parental fungal strains to permit expression of the entire pathway. This is despite the fact that fewer than that number of parental strains may be necessary depending on the how many of the necessary gene products are encoded by each heterologous nucleic acid and how many of the gene products may be functionally substituted by gene products normally expressed by the fungal strain used. For example, if the metabolic pathway requires four gene products encoded by four intronless coding sequences of about 1 kb each arranged in a contiguous cluster of about 6 kb, heterologous nucleic acids of about 1.5 kb in length will require heterokaryon panel members to contain on average four parental strains to express the pathway. But if the heterologous nucleic acids were about 3 kb in length on average, then only about 2 strains per heterokaryon on average should be sufficient to express the pathway.

But if the four coding sequences were on four physically separate chromosomes, then normally a minimum of four parental strains containing heterologous nucleic acids of at least about 1 kb on average would be needed to express the pathway because longer nucleic acids cannot encode more than one gene product. It should be noted that the 1 kb length limitation may be shortened if fragments of a given coding region were sufficient to express a functional gene product to result in expression of the pathway.

The above scenario can be further altered if one or more of the gene products can be functionally substituted by gene products normally expressed by the fungal strain used. In the immediately above example, for instance, if one of the four gene products was functionally substituted by the host fungal strain because of its endogenous metabolic activities, then normally only a minimum of three parental strains are needed to express the pathway.

Thus the number of parent strains needed per heterokaryon panel member to express a given pathway depends on 1) the number of gene products involved, 2) the size of the heterologous nucleic acids used; 3) their naturally occurring physical arrangement; and 4) the ability of the host fungal strain to functionally supply gene products necessary for expression of the pathway.

In addition to having been modified to contain heterologous nucleic acids encoding components in the metabolic pathway, as described above, the nuclei of each of the parent strains must contain a genome that results in a characteristic that renders the fungus dependent on the presence of one or more additional characteristic(s), supplied by one or more parental strain(s), for survival under the conditions used to form the heterokaryon. Thus, the nucleus of each parent confers a characteristic which would result in the failure of the fungus in which it is contained to survive under the culture conditions unless the one or more characteristic(s) is also present. For example, heterokaryons resulting from three parental strains may be selectively produced by having each strain be sensitive to the lack of a different particular nutrient that may be supplied by the culture medium. Thus only hyphal fusions that result in the presence of nuclei from all three types of parental strains, so that the deficiency of each one can be complemented by the sufficiency of the other two, can survive when all three nutrients are lacking in the medium.

For example, if three non-linked heterologous gene products are need to express a given metabolic pathway from another organism, then heterologous nucleic acids from the organism would be introduced into three parental strains, individually sensitive to the lack of nutrients X, Y and Z from the culture medium. Thus three-way fusions between these strains can be selected by culturing on media lacking X, Y and Z.

The required nutrient can be any substance which the fungus strain cell needs for growth or which, when absent, seriously impairs the ability of the fungus strain to grow or survive. Examples of useful nutrient requirements and the relevant mutants include:

(1) amino acids such as histidine (his-1 through -7 mutants), proline (aga mutants), arginine (arg-11 mutants), citrulline (arg-11 mutants), asparagine (asn mutants), choline (chol-1 and chol-2 mutants), cysteine (cys-1 mutants), glutamine (gln-1 mutants), leucine (leu-1 through -4), lysine (lys-2, -4 and -5), methionine (mac mutants and met-6, -9 and -10 mutants), and threonine (thr-2 and -3 mutants);

(2) mixtures of aromatic amino acids, such as a mixture of p-aminobenzoic acid, tyrosine, tryptophan, and phenylalanine (required by all aro strains except aro-6, aro-7 and aro-8), a mixture of tryptophan and phenylalanine (required for aro-6 mutants), a mixture of isoleucine and valine (required for ilv-1, -2 and -3), and a mixture of phenylalanine and tyrosine (required for pt mutants);

(3) vitamins such as pantothenic acid (pan-1 mutants) and thiamine (thi-2 and thi-4 mutants);

(4) purine bases such as adenine (ad-2 through ad-4 and ad-8 mutants), hypoxanthine (ad-2 and ad-3 mutants), inosine, and guanine or guanosine (gua-1 or -2 mutants);

(5) pyrimidine bases such as uracil (pyr-1 through pyr-6);

(6) saturated fatty acids (cel mutants) or unsaturated fatty acids such as $C_{16}$ or $C_{18}$ fatty acids having a double bond in the cis conformation at either the 9- or 11-position, fatty acids with a double bond in the trans configuration at the 9-position, and fatty acids with multiple cis double bonds interrupted by methylene bridges (ufa-1 and -2);

(7) physiologically important ions such as potassium (trk);

(8) sugar alcohols such as inositol (acu mutants and inl mutants) and glycerol; and (9) other organic entities such as acetate (ace mutants), I-ketoglutarate, succinate, malate, formate or formaldehyde (for mutants), p-aminobenzoic acid (pab-1, -2 and -3 mutants), and sulfonamide (sfo mutants at 35° C.).

One specific example based on a nutritional requirement is the Arg B+ gene coding for the enzyme ornithine transcarbamylase. This enzyme is present in wild type *A. niger*. Mutants lacking this enzyme (Arg B– strains) can be prepared by usual non-specific techniques, such as treatment with ultraviolet radiation, followed by screening based on an inability to grow on minimal medium, coupled with an ability to grow on a medium containing arginine. Fungi containing this genome will grow on minimal medium if they also include an ArgB+ nucleus.

Also useful for selecting for (or "forcing") heterokaryon formation are genes conferring the characteristic of resistance to any one of a variety of cytotoxic agents. For example, in an alternative embodiment, one of the parents can have a requirement for a nutrient while another has resistance to a toxic effect induced by a noxious chemical, an antibiotic or virus, or a harsh environmental conditions such as a predetermined temperature range to which the other parent is sensitive.

Specific examples of noxious chemicals that can exert a toxic effect include acriflavine (resistance conferred by acr generally, with the presence of the shg gene being required for resistance by acr-4 and acr-6); 3-amino-1,2,4-triazole (resistance conferred by acr-2, atr-1, cpc, leu-1 or leu-2)); dyes such as malachite green (resistance conferred by acr-3); caffeine (resistance conferred by caf-1); purine analogs (resistance to 8-azaadenine and 2,6-diaminopurine conferred by aza-1; resistance to 8-azaadenine and 8-azaguanine conferred by aza-2; resistance to 8-azaguanine and 6-mercaptopurine conferred by aza-3; resistance to 6-methylpurine conferred by mep(3) and mep(10); cyanide (insensitivity conferred by cni-1 in the first 24 hours of growth); tetrazolium (resistance conferred by cya-6 and cya-7); cycloheximide (resistance conferred by cyh-1, -2 and -3); chromate (resistance conferred by cys-13); 2-deoxy-D-glucose (resistance conferred by dgr⁻); edeine (resistance conferred by edr-1 and -2); ethionine (resistance conferred by eth-1, by nap in the presence of p-fluorophenylalanine, and by oxD if the ethionine is in the D form); fluoro compounds such as 5-fluorodeoxyuridine, 5-fluorouracil, and 5-fluorouridine (resistance to all three conferred by fdu-2; resistance to 5-fluorouracil being conferred by uc-5 in an ammonia-free minimal medium; resistance to 5-fluorodeoxyuridine and 5-fluorouridine being conferred by ud-1), and fluorophenylalanine (resistance conferred by fpr-1 through -6 under certain conditions); 8-azaadenine (resistance conferred by mts); methyl methane sulfonate (insensitive or marginally sensitive for upr-1); surface-active agents such as dequalinium chloride, cetyltrimethyl ammonium bromide, and benzalkonium chloride (resistance conferred by sur-1); and metal ions such as vanadate (resistance conferred by van).

Examples of antibiotics typically exerting a toxic effect include benomyl [methyl-1-(butylcarbamolbenzimidazol-2-yl carbamate] (resistance conferred by Bml); antimycin A (insensitivity conferred by cni-1 in the first 24 hours of growth); polyene antibiotics such as nystatin (resistance conferred by erg-1 and -3); and oligomycin (resistance conferred by oli).

Also useful are genes conferring resistance to extremes in various environmental conditions such as a high or low temperature, the lack of oxygen (resistance conferred by an), constant light (resistance conferred by lis-1, -2 and -3) or the absence of light, UV radiation, ionizing radiation, and high or low osmotic pressures. In a particularly preferred embodiment, the resistance to a toxic effect is a resistance to an antibiotic such as ampicillin.

Strains generally useful in the invention can be grown on 1× Vogel's Minimal Medium (N medium) in cotton-plugged test tubes, with supplements being added depending on the phenotype of the strain, such as, for example, histidine; arginine and/or inositol. Typical strains may be obtained, for example, from the Fungal Genetics Stock Center ("FGSC") and from D. D. Perkins, Stanford University. Another *N. crassa* strain believed to be useful is M246-89601-2A (obtained from Dr. Mary Case, University of Georgia, Athens). This strain is a derivative of wild-type 74A, which contains a stable qa-2 mutation (M246), an arom-9 mutation (M6–11), and an inos (io601) mutation. The double mutant qa-2, arom-9, lacks both the biosynthetic and catabolic dehydroquinase activities and is unable to grow on minimal medium without a supplement of aromatic amino acids, such as, for example, phenylalanine at a concentration of about 80 µg per ml.

Useful strains of *A. niger* (ATCC 46951) are also available from the Fungal Genetics Stock Center, as well as strains of Fusarium, Gelasinospora, and *Sordaria fimicola*, or can be prepared by mutagenizing with UV light to form an isolate that requires ornithine or arginine for growth in a defined minimal media. This strain, which lacks ornithine carbamoyl transferase, has been called arg B (350(-)52). Media for growing *A. niger* or *A. nidulans* are described by Cove, *Biochim Biophys Acta* (1966) 113:51–56.

Standard procedures are generally used for the maintenance of strains and the preparation of conidia (Davis and de Serres, *Methods Enzymol* (1971) 17A:79–141). Mycelia are typically grown in liquid cultures for about 14 hours (25° C.), as described in Lambowitz et al. *J Cell Biol* (1979) 82:17–31. Host strains can generally be grown in either Vogel's or Fries minimal medium supplemented with the appropriate nutrient(s), such as, for example, histidine; arginine; phe, tyr, and/or trp (each about 80 µg per ml); p-aminobenzoic acid (about 2 µg per ml); and inositol (about 0.2 mg per ml).

Many fungal strains with the desired characteristics are publicly available. If not readily available, however, one of ordinary skill in the art can use, without undue experimentation, selection techniques well-known in the art for separating out either the desired mutants or the engineered nuclei providing the desired characteristic. Illustrative two-member parental combinations are shown in the table below.

TABLE 2

| First Nucleus | | Second Nucleus | | |
|---|---|---|---|---|
| First Characteristics | Second Property | Second Characteristic | First Property | Fusion Conditions |
| his⁻ | arg⁺ | arg⁻ | his⁺ | minimal medium (mM) |
| his⁻ | bmʳ | bmˢ | his⁺ | MM + bm |
| cyclohexˢ | bmʳ | bmˢ | cyclohexʳ | MM + bm + cyclohex |
| caffeineˢ | arg⁺ | arg⁻ | caf-1 | MM + caffeine |
| Thi-2 | wt | aro-6 | wt | MM + thiamine + trp + phe |

As seen in the table, a variety of complementary characteristic/property combinations can be chosen to fit various fusion conditions. In general, the nutrient requirement is manifested by a mutant strain, while the ability to resist certain substances may more conveniently be conferred by modification of the nucleus with an expression system for the resistance gene. Alternatively, the nutritional requirement can be effected using recombinant techniques such as homologous recombination with a transforming vector and the resistance can be conferred by mutation under conditions where the toxic conditions are present.

In one embodiment of the invention, host cells are converted to spheroplasts for transformation. When spheroplasts are used, a preferred method or preparing them is by enzymatic digestion of the cell walls, for example, by using a chitinase/glutamase mixture. The selection of a suitable enzyme for enzymatic digestion is within the skill of the art. Useful enzymes are those capable of digesting complex polysaccharides, and are found among those known as effective in preparing fungal spheroplasts of a wide variety of fungal species. Specific examples of suitable enzymes include Novozym 234 (an impure mixture of enzymes) and J-glucuronidase. Other suitable methods may be used to form spheroplasts. If suitable methods for cell wall penetration by the use of vectors are identified, however, whole cells of the fingal host may be used along with or instead of spheroplasts.

To modify the nucleus of the first fungus host strain to contain and express a heterologous nucleic acid, the practice of the invention employs, unless otherwise indicated, molecular biology, microbiology, and recombinant DNA techniques that are well within the skill of the art. Such techniques are explained fully in the literature. See, e.g., Maniatis et al., *Molecular Cloning: A Laboratory Manual*

(1982); D. N. Gover et al. *DNA Cloning: A Practical Approach* (1985) Volumes I and II; *Oligonucleotide Synthesis* (M. J. Gait ed. 1984); *Nuclei Acid Hybridization* (Hames et al. eds. 1985); *Transcription and Translation* (Hames et al. eds. 1984); *Animal Cell Culture* (R. I. Freshney ed. 1986); *Immobilized Cells and Enzymes* (IRL Press 1986); B. Perbal, *A Practical Guide to Molecular Cloning* (1984).

General Procedure for Transformation of *N. crassa*

As explained above, the population of heterologous nucleic are used to transform parent host strains of a filamentous fungus, such as described by Stuart, "Heterologous dimeric proteins produced in heterokaryons." Strains of *Neurospora crassa* are publicly available from the Fungal Genetics Stock Center, but independently prepared strains can also be used. Mutants may be isolated de novo, as illustrated by Stadler et al. *Genetics* (1966) 54:677–685 and Haas et al. *Genetics* (1952) 37:217–26. Useful strains can also be obtained from D. D. Perkins from Stanford University. Strains are typically grown on 1X Vogel's Minimal Medium ("N medium") in cotton-plugged test tubes, with appropriate supplements being added depending on the strain's phenotype.

Spheroplasts are used as subjects for transformation. To form conidial spheroplasts, the fungus is inoculated onto 25 ml of solid N medium, with appropriate supplements in four to five 125-ml Erlenmeyer flasks, which have been plugged with cotton. The cultures are grown at room temperature for 5–7 days.

The conidia are harvested by adding 10 ml of N medium to each flask, replacing the cotton plug, and swirling the flask. The solids are allowed to settle for a few minutes. The conidial mixture is poured to an autoclaved cheesecloth bag hanging in the mouth of an Erlenmeyer flask and secured with one or more rubber bands. The filtrate is recovered, and the concentration of conidia is determined by a hemocytometer count, with chains being counted as one.

A volume of $2\times10^9$ conidia is added to 150 ml of liquid N medium containing 1.5% sucrose and appropriate supplements. The conidia are germinated in the cotton-plugged flask while shaking (150–200 rpm) for 5–6 hours at room temperature until more than 75% have germinated and the germ tubes are 1–4 conidial diameters in length. The cells are harvested by centrifuging at about 1500–2000 rpm for 10 minutes. The cell pellet is rinsed three times with water.

The pellet is then re-suspended in 10 ml of 1.0 M sorbitol, and the spheroplasts are prepared by enzymatic removal of the tough conidial cell wall with an enzyme under isotonic conditions, to prevent the "bursting" of the spheroplasts as they are formed. The protocol is adapted from the method of Vollmer and Yanofsky, *Proc Natl Acad Sci USA* (1986) 83:4869–73.

Specifically, in a sterile 250 ml Erlenmeyer flask, the conidial suspension is generally added to 50 mg of a solid enzyme sold by Novo Laboratories under the trade name Novozym 234. The mixture is shaken (100 rpm) at 30° C. for about an hour (±10 minutes) to digest the cell wall. The spheroplast formation process is monitored by examining a small aliquot of the mixture microscopically under a cover slip. Spheroplasts can be detected because they lyse osmotically when water is applied to one end of the cover slip. The process should be monitored frequently at the later stages of spheroplast formation.

The spheroplast mixture is decanted into a sterile 15-ml conical centrifuge tube, and the spheroplasts are recovered by centrifuging at 500 rpm (10 minutes) in a swinging bucket table top centrifuge. The resulting pellet is rinsed twice with 10 ml of 1.0 M sorbitol and then once with the following STC solution: 91 g sorbitol; 50 mM Tris-HCl; 50 mM $CaCl_2$; sufficient NaOH to adjust the pH to 8.0; and q.s. to 500 ml.

The final spheroplast pellet is suspended in a mixture of 16.0 ml STC, 200 U1DMSO, and 4 ml of the following PTC solution: 200 g polyethylene glycol sold under the trade name "4000" by Sigma; 50 mM Tris-HCl; 50 mM $CaCl_2$; sufficient NaOH to adjust the pH to 8.0; and q.s. to 50 ml.

The resulting suspension of spheroplasts can either be used directly or stored frozen in 1.0 ml aliquots at −80° C.

In a sterile, 15-ml screw-cap tube, 2.0 μl of 50 mM Spermidine solution, 5.0 μl of the plasmid DNA to be transfected, such as that containing the heterologous nucleic acid along with a selectable marker such as benomyl resistance (usually at a concentration of about 1.0 mg/ml) and 5.0 μl of a 5 mg/ml heparin solution are mixed by flicking the tube. The spermidine solution is prepared by dissolving 12.73 mg of spermidine in 1.0 ml TE and adjusting the pH to 8.0, and can be stored at −20° C. The heparin solution is prepared by dissolving 50 mg of the sodium salt of heparin in 10 ml of STC and can be stored in frozen aliquots.

The contents of the tube are briefly spun (pulsed) in a tabletop centrifuge and then placed in an ice bath. About 50–100 μl of thawed spheroplasts are added to the tube. The mixture is then incubated on ice about 30 minutes, but incubation periods of about 20 minutes on ice have been successful. About 1 ml of PTC is added and mixed well by flicking the tube. The mixture is incubated further at room temperature for about 20 minutes.

A Regeneration "Top" Agar is prepared by mixing: 20 ml 50× Vogel's Minimal Medium; 825 ml of water; 182 g sorbitol; and 28 g agar. The top agar is autoclaved and 100 ml of a 10× FIGS solution (containing 5 g/l fructose, 2 g/l inositol, 2 g/l glucose, and 200 sorbose) is added. 15 ml of the top agar is incubated at 50–55° C. and poured into the tube containing the spheroplasts and plasmid DNA. The contents are quickly mixed by flicking and inverting the tube 2–3 times and then uniformly poured onto a layer of plating "bottom" agar.

The "bottom" agar is prepared by mixing any required supplements, in 1×N medium; autoclaving; and adding 10×FIGS and benomyl (if benomyl resistance is used as a marker) to final concentrations of 1× and 0.5 μg/ml respectively. A volume of 25 ml of "bottom" agar is poured into a petri plate and allowed to harden.

After the top agar has been poured over the bottom agar, bubbles are removed by flaming. The plates are kept in an upright position until the top agar has solidified (about 5 minutes). If the top agar tends to harden prematurely, the bottom agar plates can be prewarmed. Once the top agar has solidified, the plates are incubated in an inverted position at 30° C.

For selection of the *N. crassa* transformants, the host is thus cultured on the appropriate medium (having composition only the transformed cells can utilize or containing an antibiotic to which only transformed cells are resistant) and incubated at about 34° C. An indication of a successful transformation can be seen about 24–36 hours after plating. Stable transformants are generally scored after three days of growth. The incubation period to detect transformants will vary depending on the host strain and the phenotypic marker.

Selected transformants can be screened for, expression of the heterologous nucleic acid by standard methods, such as an appropriate ELISA, a colony blot immunoassay, restriction enzyme analysis, filter hybridization, nested deletion subcloning, and the like.

In the present invention, the above-described recombinant techniques are used to produce parental fungal strains each 1) transformed to contain a heterologous nucleic acid, and 2) having a characteristic that negatively affects growth under specified conditions but is correctable by one or more characteristic(s) conferred by one or more additional parental strain(s). The resulting parental strains are used to form the heterokaryon panel members.

Alternatively, electroporation procedures can be used to transform freshly harvested conidia of filamentous fungus such as *Neurospora crassa* (Van, D. C. *Fungal Genetics Newsletter No.* 42A (Supplement) (1995)). In general, conidia are harvested from 7–28 day old cultures. The cells are washed in 1 M sorbitol solution and suspended at a final concentration of $2.5 \times 10^9$ cells/ml. Approximately 5 µg of linearized DNA is added to an aliquot of the conidial suspension and a portion of this is placed in the bottom of an electroporation cuvette, for example an electroporation cuvette with a 0.2 cm gap. An electroporator, such as an In Vitrogen Electroporator II, is set with a voltage gradient of about 7.25 kV/cm and a setting of about 71 µF and about 200 ohms. Following electroporation, the cells are plated on appropriate media with or without a top agar essentially as described above.

Following transformation, a stable parental strain containing the heterologous nucleic acids as a library may be established by expanding the culture on selective media for the particular host cell used with each parental strain.

Production of the Heterokaryon

Because the parental fungal strains are chosen to be homozygous with respect to all heterokaryon compatibility alleles (with the exception of the mating allele when the tol gene is present as explained above), co-culturing of parental strains under conditions wherein none can survive alone permits the selection of fused fungi so that the heterokaryotic fungus of the invention is formed. By hyphal fusion, different haploid nuclei of different parental fungi come to coexist in a common cytoplasm. While not wishing to be bound by any theory, it is believed that membrane fusion results from the aggregation of intramembranous particles within each cell, making possible cell contacts between protein-free areas. Rearrangement of the lipids in the contact areas then leads to full fusion.

Because each of the parental strains contains a nucleus which produces one or more different heterologous gene product(s), the resulting heterokaryon is capable of expressing all or part of a heterologous metabolic pathway.

The heterokaryon thus generated is stable, with the different nuclei dividing at about the same rate. When heterokaryons having two (or more) nuclei are formed, it is possible to form some mononucleated hybrid cells if the nuclei enter mitosis at approximately the same time as they fuse. This type of nuclear fusion yields heterozygous diploid nuclei when it occurs, but it is rare, and the diploid nuclei formed are usually greatly outnumbered by the haploid nuclei.

Panel of Heterokaryons

The compositions and methods of the present invention employ a panel of heterokaryons. As described above, the panel comprises two or more heterokaryons, each heterokaryon being capable of expressing at least two heterologous nucleic acids. The preferred panels of the present invention will contain more than two members, the more preferred containing more than ten members, the most preferred containing more than twenty members. One example of the panel of heterokaryons is a panel that produces penicillin. For example, to generate such a panel, conidial suspensions of individual strains, each containing a heterologous nucleic acid from *P. notatum* known to be involved in penicillin expression for example, are mixed in a matrix using a microtiter plate or other convenient format.

Alternatively, the panel can comprise a random mix of parental strains as opposed to the strains containing known or characterized nucleic acids. In such an arrangement, the panel will comprise two or more homokaryons in a random array. After fusing, the resulting heterokaryons are arrayed to form a panel of heterokaryons that expresses penicillin.

As described previously, the microtiter plate contains minimal medium (without agar if in liquid form) which will not support the growth of any parent strain alone but which will support the growth of a heterokaryon culture composed of nuclei from each of the different parental strains used. For example, if each of the fusing parental fungal strains carry an auxotrophic requirement different from the other, the only cells capable of growing in culture media where each of the nutrients are absent will be complementary heterokaryons which are also capable of expressing the heterologous nucleic acids in the parental strains. For example, three strains may require the presence of three different amino acids while another strain may require a base, such as adenine. Each strain can be independently maintained on media supplemented with the appropriate extra metabolite, but neither strain can survive alone on minimal media. Heterokaryons containing nuclei from all four strains, however, will survive on minimal media because each nucleus complements the other's requirement.

A typical minimal medium contains: per liter, 5.0 g Dextrose, 50.0 ml of a Salt Solution (below), 1.0 ml trace elements (below), and 12.5 g Agar (adjusted pH 6.5) if the media is to be in solid form. The Salt Solution contains: 120.0 g $NaNO_3$, 10.4 g KCl, 10.4 g $MgSO_4$, and 30.4 g $KH_2PO_4$.

The trace element solution contains: 1.1 g $(NH_4)_6Mo_7O_{24}.4H_2O$, 11.0 g $H_3BO_3$, 1.6 g $CoCl_2.6H_2O$, 1.6 g $CuSO_4$, 50.0 g $Na_2EDTA$, 5.0 g $FeSO_4.7H_2O$, 5.0 g $MnCl_2.4H_2O$, and 22.0 g $ZnSO_4.7H_2O$ (pH 6.5).

Thus, to maintain the heterokaryotic filamentous fungus in its heterokaryotic state, external forcing is maintained. Growing the heterokaryotic fungal cells on minimal media "forces" the strains to remain together. If mating types are opposite, the presence of the tol gene can be used to maintain stable (A+a) heterokaryons.

The combinatorial metabolic pathway is produced by culturing the panel heterokaryons of the invention under conditions favorable to expression of the pathway. Any resultant pathway component(s), including primary or secondary metabolite(s), of interest may be recovered from the culture and purified in accordance with standard techniques adapted, of course, as necessary to preserve the structure and finction of the pathway component.

Preferably, the heterokaryotic filamentous fungus carries an expression unit that allows the host being cultured to secrete the desired pathway component directly into a minimal growth medium, so that the component can be purified directly from cell-free medium. Intracellularly produced components can be isolated from cell lysates. Useful purification methods in accordance with known procedures are within the skill of the art, such as, for example, molecular size exclusion, ion-exchange chromatography, HPLC, affinity chromatography, hydrophobic interaction chromatography, and the like.

Because of the combinatorial power available from the production of heterokaryon panels, the instant invention provides an efficient means of rapidly generating combinatorial metabolic pathways for use in high-throughput screening methods to detect novel and useful metabolites or catabolic activities.

Assay for Secreted Metabolites

Microtiter plates are commercially available which are sterile, contain filters of known sizes in the bottom of each well (e.g. 0.6 micron or 0.45 micron pore sizes) and which, when placed on a commercially available vacuum filter holder will deposit liquid media through the filter, into a second identically configured microtiter plate, keeping the media in the same order as the cells and the culture plate all the while maintaining the sterility of the original heterokaryon culture in the original culture plate.

The collected media can be tested for the presence of a desirable metabolite, increased or decreased metabolic activity, binding, toxicity or any other characteristic which can be measured. During this testing activity, the original fungal heterokaryotic cell cultures can be stored at 4° C. or, if the testing is expected to require more than a week, the culture plate can be stored frozen with or without a cryopreservative added.

Upon identification of a culture that is producing a desirable metabolite, the cells can be removed from the culture plate and cultured on solid medium and after sufficient growth used to inoculate an expanded liquid culture. Alternately, and where the heterologous nucleic acids were known or previously characterized, the original strains used to form the panel can be mixed directed together as used for an expanded culture. When grown under whatever the optimal conditions are for the particular fungal host used, this expanded host culture will produce the desired metabolite in sufficient quantities for further research evaluation or use.

Assay for Non-Secreted Metabolites

If the metabolite is not secreted, a portion of the cell mass of each heterokaryon panel member can be removed, disrupted by standard methods and the cell supernatant and debris assayed for the desirable metabolite. Once the panel member that produces the desired metabolite has been identified, another portion of the cell mass from the panel member can be used to make an expanded culture. Again, when grown under optimal conditions for the particular heterokaryon, this expanded host culture will produce the desired product in sufficient quantities for further evaluation and use.

Other Uses for a Heterokaryon Panel

The heterokaryon panel of the present invention can also be used to isolate heterologous nucleic acids encoding components in a metabolic pathway. In such a use, the heterologous nucleic acids present in an individual heterokaryon panel member can be isolated after detecting expression of a desired metabolic pathway. Although the panel member may contain heterologous nucleic acids unrelated to the pathway, the panel member will also contain one or more heterologous nucleic acids encoding gene products that permits pathway expression. Either 1) characterization or 2) further cycles of combinatorial metabolic library formation will permit the identification of the pathway related nucleic acids.

With characterization, the individual nucleic acids can be screened for the presence of coding sequences followed by comparisons of those sequences with known sequences to infer possible functionality of the encoded gene product. Those nucleic acids encoding gene products likely to be related to the metabolic pathway of interest can be individually introduced into parental fingal strains for the formation of additional heterokaryons to express the pathway. In the event that the pathway is not reproduced, other characterized nucleic acids can also be introduced into parental strains to produce heterokaryons containing more of the isolated heterologous nucleic acids.

For example, if a heterokaryon panel member is identified as producing a desired secondary metabolite and isolation and characterization of the heterologous nucleic acids found therein reveals 10 coding regions six of which appear to encode gene products required for expressing the pathway, the six coding regions can be introduced into fungal host strains as expression units. Following fusion and selection for heterokaryons containing all six coding regions, detectable expression of the pathway permits further fusions comprising different combinations of the six coding regions to determine the minimum needed to express the pathway. Alternatively, if no pathway expression is detectable after fusion, then one or more of the additional four coding regions can be individually introduced into the heterokaryon panel to re-establish expression of the pathway. If further necessary, isolated heterologous nucleic acids not identified as possessing a coding region can also be individually introduced into the heterokaryon panel to re-establish expression of the pathway.

With further cycles of combinatorial metabolic library formation, the isolated heterologous nucleic acids are not characterized but are used again to transform host cells, with or without further fragmentation or ligation to regulatory elements, for the production of additional heterokaryon panels. By again selecting for heterokaryons expressing the pathway and/or arising from fusion of the same or a lower number of parental strain nuclei, repeated cycles of this method will produce heterokaryons having a decreasing content of heterologous nucleic acids until further cycles results in no pathway expression. Isolation and characterization of the heterologous nucleic acids from previous panel members able to express the pathway will result in the identification of nucleic acids likely to encode components required for the pathway. Individual combinations of these isolated nucleic acids will confirm their role in pathway expression.

The above methods comprise mere repetition of steps well known in the art of molecular biology and biochemistry. As such, no undue experimentation is necessary because the steps merely isolated and identify the nucleic acids responsible for the needed pathway components while excluding nucleic acids unrelated to the pathway. Given the existence of components needed to express a metabolic pathway as established with the first heterokaryon detected as expressing the pathway, the above methods are routine manipulations that do not involve any significant level of unpredictability or de novo experimentation.

Kit Containing Heterokaryon Panels

The present invention further provides kits containing one or more containers that contain a heterokaryon panel of the present invention. As used herein, a container refers to a physical device into which cells can be placed and stored. The preferred container contains an array into which the panel can be placed for culturing or storage. One example of such a container is a 96 well microtiter plate. A skilled artisan can readily adapt any of the available container means so that it holds a heterokaryon panel of the present invention.

The following examples are intended to illustrate but not to limit the invention.

All references cited above are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A combinatorial metabolic library comprising a plurality of heterologous nucleic acids from one or more species of source organism wherein the nucleic acids are capable of expressing all or part of a metabolic pathway in a host cell.

2. A panel comprising two or more cells wherein each cell contains a portion of the library of claim 1.

3. A panel of claim 2 wherein the cells are fungal cells.

4. A panel comprising two or more heterokaryonic cells wherein each of said heterokaryonic cells contains a portion of the library of claim 1.

5. A panel of claim 3 or 4 wherein the cells are selected from the groups Phycomycetes, Ascomycetes, Basidiomycetes, and Deuteromycetes.

6. A panel of claim 5 wherein the cells are filamentous fungal cells.

7. A panel of claim 6 wherein the cells are selected from the group consisting of *N. intermedia, N. crassa, N. sitopula, N. tetraspora, A. nidulans, A. niger, A. terreus*, and *A. fumegatus*.

8. A panel of claim 7 wherein the filamentous fungal cells are *Neurospora crassa* cells.

9. A panel of claim 4 wherein each heterokaryonic cell is formed by fusing two or more parental fungal strains, wherein said heterokaryon requires the presence of each parent fungal nuclei for survival, each parental fungal strain containing a heterologous nucleic acid present in one or more cells of the panel.

10. A panel of claim 4 wherein one or more heterokaryonic cell secrets a metabolite produced by the expressible metabolic pathway.

11. A kit comprising one or more containers that contains the heterokaryon panel of claim 4.

12. A method for producing a panel of heterokaryons comprising two or more heterokaryons wherein each of said heterokaryons contains at least two heterologous nucleic acids encoding a component of a metabolic pathway, comprising the steps of:

fusing two or more parental fungal strains, each strain containing a heterologous nucleic acid molecule that encodes a component of a metabolic pathway and where said parental strains are homozygous for all heterokaryon compatibility alleles and selecting two or more heterokaryons thus formed to generate said panel, wherein said heterokaryons requires the presence of each parental fungal nuclei for survival.

13. The method of claim 12 wherein at least one heterokaryon in the panel expresses all or part of a metabolic pathway requiring the expression of at least one heterologous nucleic acid.

14. The method of claim 13 wherein said metabolic pathway produces a secreted metabolite.

15. The method of claim 12 wherein said parental fungal strains are fused using a pulsed electric field.

16. A method for screening a heterokaryon panel for expression of a desired metabolite comprising culturing the heterokaryon panel of claim 4 under conditions in which the heterologous nucleic acids are expressed; and screening the panel to identify a heterokaryon which produces the metabolite.

17. The identified heterokaryon of claim 16.

18. A method for producing a desired metabolite, said method comprising the step of culturing the heterokaryon of claim 17 under conditions which produces the metabolite.

19. A method for screening a heterokaryon panel for expression of a desired catabolic activity comprising culturing the heterokaryon panel of claim 4 under conditions in which the heterologous nucleic acids are expressed; and screening the panel to identify a heterokaryon which expresses the catabolic activity.

20. The identified heterokaryon of claim 19.

21. A method for degrading a substance with a catabolic activity expressed in a heterokaryon panel member, said method comprising combining the substance with the identified heterokaryon of claim 20; and culturing under conditions which expresses the catabolic activity.

22. A method for identifying nucleic acids encoding components of a metabolic pathway comprising isolating heterologous nucleic acids from the identified heterokaryon of claim 17; and screening them for nucleic acids encoding components of the pathway.

* * * * *

UNITED STATES PATENT AND TRADEMARK OFFICE
CERTIFICATE OF CORRECTION

PATENT NO.     : 6,268,140 B1
DATED          : July 31, 2001
INVENTOR(S)    : W. Dorsey Stuart It is certified that error appears in the above-identified patent and that said Letters Patent is hereby corrected as shown below:

<u>Title page,</u>
Item [63], Related U.S. Application Data, should be deleted.

<u>Column 1,</u>
Lines 3-11, should be deleted.

Signed and Sealed this

Nineteenth Day of August, 2003

JAMES E. ROGAN
*Director of the United States Patent and Trademark Office*